(12) United States Patent
Edmonson et al.

(10) Patent No.: US 7,229,821 B1
(45) Date of Patent: Jun. 12, 2007

(54) ACOUSTIC WAVE RFID/BIOSENSOR ASSEMBLIES

(75) Inventors: Peter J. Edmonson, Hamilton (CA); William D. Hunt, Decatur, GA (US); Desmond D. Stubbs, Riverdale, GA (US); Stephen T. Makk, Toronto (CA)

(73) Assignee: P.J. Edmonson Ltd., Hamilton, Ontario (CA)

( * ) Notice: Subject to any disclaimer, the term of this patent is extended or adjusted under 35 U.S.C. 154(b) by 0 days.

(21) Appl. No.: 11/354,814

(22) Filed: Feb. 16, 2006

(51) Int. Cl.
   *C12M 3/00* (2006.01)
   *H01L 41/00* (2006.01)
(52) U.S. Cl. .............................. 435/287.1; 435/287.2; 310/311; 310/313 R; 310/340; 310/341; 310/343
(58) Field of Classification Search .................... None
   See application file for complete search history.

(56) References Cited

OTHER PUBLICATIONS

David Crane, SPLAT: Explosives/Chemical Weapons-Detection Tech Meets Paintball, www.defensereview.com, Aug. 16, 2004, 2 pages.

*Primary Examiner*—Christopher L. Chin
(74) *Attorney, Agent, or Firm*—Robert F. Delbridge

(57) ABSTRACT

A deployable acoustic wave RFID/biosensor assembly has at least one protective layer, and an acoustic wave RFID/biosensor within the protective layer or layers. The acoustic wave RFID/biosensor includes an acoustic wave device, a biolayer mounted on the acoustic wave device, an electric circuit operable to actuate the acoustic wave device, and a fluidic chamber associated with the biolayer. In use, the fluidic chamber contains fluid which, if a predetermined substance to be sensed is present, operates to modify the biolayer which in turn affects the operation of the acoustic wave device. Protective fluid is provided within the protective layer or layers substantially surrounds the acoustic wave RFID/biosensor to protect the acoustic wave RFID/biosensor from damage when the RFID/biosensor assembly impacts a target and to protect the biolayer from deterioration during storage and use.

8 Claims, 5 Drawing Sheets

ACOUSTIC WAVE RFID/BIOSENSOR ASSEMBLIES

FIELD OF THE INVENTION

This invention relates acoustic wave RFID/biosensor assemblies.

BACKGROUND OF INVENTION

Improvised explosive devices (IEDs) are becoming the defacto standard for terrorist or paramilitary groups. The devices can be buried, concealed or disguised as everyday objects and left at transportation links or other populated or strategic places for surreptitious destruction. Chemical agents may be included within these devices to cause maximum threat potential. A suspect IED can halt all activity in the surrounding area for some time as the authorities determine the nature of the threat. Quite often, a remote explosive or biological detector has to be transported to the site to determine if the device is a positive threat. If the suspected IED is positioned in an awkward place, such as high up in a luggage rack of a train or in the luggage compartment of a bus, a remote detector may have difficulty accessing the suspected IED. In some cases, a human need to approach the device at an unsafe close distance to determine if the device is a positive threat. Vehicle convoys cannot stop and have every potential IED checked by either a remote detector or individuals. Such vehicles also need approximately 400 meters of detection distance when reaction times, safe standoff distances and speeds of 100 kph are all taken into account.

A recent special issue on sensors for the prevention of terrorist acts was published in the IEEE Sensors Journal, a publication of the IEEE Sensors Council, Volume 5, No. 4, August, 2005. Numerous methods for the detection of biological, explosive and chemical threats are described. However, known field portable units compromise detection performance to yield their small handheld size. Detection methods utilizing ion mobility spectroscopy (IMS), mass spectrometry (MS), gas chromatography (GC), Raman spectroscopy (RS), fiber-optic sensors and microwave spectroscopy all have the same problem with detecting substances at a distance in inaccessible positions.

Professor Loc Vu-Quo of the Mechanical and Aerospace faculty of the University of Florida has led a team of graduate students who have demonstrated the feasibility of using a consumer-off-the-shelf (COTS) paintball gun to fire a wireless Sticky Polymer Lethal Agent Tag (SPLAT) onto an intended target from a safe distance of approximately 20 meters away.

Biosensors as described by (W. D. Hunt et al "Time-dependent signatures of acoustic wave biosensors," *IEEE Proceedings*, Vol. 91, no. 6, pp. 890-901, June 2003), (D. D. Stubbs, et al "Investigation of cocaine plumes using surface acoustic wave immunoassay sensors," *Analytical Chemistry*, vol. 75, no. 22, pp. 6231-6235, Nov. 15, 2003), (Sang-Hun Lee et al "Real-Time Detection of Bacteria Spores Using a QCM Based Immunosensor," *Proceedings IEEE Sensor Symposium,* 2003) and (Sang-Hun Lee et al "Vapor Phase Detection of Plastic Explosives Using a SAW Resonator Immunosensor Array" *Proceedings IEEE Sensor Symposium,* 2005) have been successfully assembled by immobilizing a monolayer of antibodies onto the surface of an acoustic wave (AW) device.

SUMMARY OF THE INVENTION

According to the present invention, a deployable acoustic wave RFID/biosensor assembly has at least one protective layer and an acoustic wave RFID/biosensor within the protective layer or layers. The acoustic wave RFID/biosensor includes an acoustic wave device, a biolayer mounted on the acoustic wave device, an electrical circuit operable to actuate the acoustic wave device, and a fluidic chamber associated with the biolayer. In use, the fluidic chamber contains fluid which, if a predetermined substance to be sensed is present, operates to modify the biolayer which in turn affects the operation of the acoustic wave device. Protective fluid is provided within the protective layer or layers substantially surrounding the acoustic wave RFID/biosensor to protect the acoustic wave RFID/biosensor from damage when the RFID/biosensor assembly impacts a target and to protect the biolayer from deterioration during storage and use.

The at least one protective layer may comprise a protective outer layer containing protective fluid to protect the acoustic wave RFID/biosensor from damage when the RFID/biosensor assembly impacts the target, and a protective inner layer containing protective fluid which protects the biolayer from deterioration during storage and use.

The protective outer and inner layers may be substantially spherical.

The protective outer layer may be adapted to rupture when the RFID/biosensor assembly impacts a target to cause leak of fluid therefrom, said leaking fluid being selected such that it causes the RFID/biosensor assembly to adhere to the target.

The acoustic wave RFID/biosensor may include a power source to provide power for the electrical circuit and which in use improves the temperature and/or humidity environment of the biolayer. The acoustic wave RFID/biosensor may include a blackbody radiator to provide a passive convectional pump which causes fluid in the fluidic chamber to pass over the biolayer.

The RFID/biosensor assembly may have an aerodynamic shape which, when the RFID/biosensor assembly is deployed, causes the RFID/biosensor assembly to follow a predicted trajectory path to an intended target.

An RFID/biosensor assembly in accordance with the invention may comprise discharging the RFID/biosensor assembly from the barrel of a gun.

This invention improves upon the manner in which an RFID/biosensor can be deployed to detect a wide variety of chemicals and biological molecules. One of the major problems that this invention addresses is how to devise RFID/biosensor systems so that the sensors can be positioned where they would detect a threat. This invention also addresses the issue of the sensor's longevity and survival of any impact during positioning. Improvements described in this application enable RFID/biosensors to be easily reconfigured to suit the needs of several detection systems. Some system configurations include (i) remotely positioned RFID/biosensor units with energy sources to activate vapor sampling, warning alerts and other electrical circuitry, (ii) remotely positioned RFID/biosensor units with a passive backscatter RF link to communicate the alert and (iii) operator handheld or operator positioned networked units using a modification of the components within configurations (i) and (ii).

The core of such systems is an acoustic wave device configured as a passive radio frequency (RF) backscatter unit with an identification (ID) code embedded within the structure of the device. An immobilized monolayer of antibodies is then placed on the surface of the acoustic wave device which reacts with selected chemicals and biological molecules depending on the structure chosen for the antibodies. Such an RFID/biosensor has been described by P. J. Edmonson et al., "A SURFACE ACOUSTIC WAVE SENSOR OR IDENTIFICATION DEVICE WITH BIOSENSING CAPABILITY", U.S. patent application Ser. No. 11/139,477, filed May 31, 2005, the contents of which are hereby incorporated herein by reference.

This invention permits RFID/biosensors to be deployed from a safe standoff distance to a potential threat without placing the operator or other entities in harm's way. Standoff distances are defined by the perceived threat being investigated and may vary from tens to hundreds of meters. Speed of deployment is also critical where logistics or physical placement of the threat may prevent the deployment of robotic type apparatus to position a sensor near the threat object. This invention provides a low cost yet accurate deployment strategy to place RFID/biosensors in close proximity to a threat object or perceived threat area using simple ballistic techniques and to maintain a high degree of confidence that the sensor system will be operational for a specified amount of time after deployment.

Double protection is provided with this invention to ensure that the RFID/biosensor system will survive impact and be operational for a specified period of time. The invention first improves the time duration and longevity of the immunosensor portion of the RFID/biosensor during storage and operational use. By enclosing the immunosensor portion of the RFID/biosensor within fluid filled compartments, the environmental storage range and shelf life of the RFID/biosensor is further prolonged. Selective fluids within the compartments prolong the longevity of the immunosensor portion of the RFID/biosensor such that the fluid prevents the immunosensor portion from dehydrating. RFID/biosensor longevity is further improved by including components within the RFID/biosensor module which control the temperature and humidity within the volume immediately surrounding the immunosensor portion of the RFID/biosensor during its operational phase.

Secondly, this invention can ensure that the RFID/biosensor module survives the extreme impact from being launched via ballistics, dropped or placed from distances greater than several hundred meters. Fluid filled compartments surrounding the RFID/biosensor module can minimize the deceleration forces upon impact. Thus, the invention enables an RFID/biosensor to be rapidly deployed onto a target that may be up to several hundred meters away and function reliably upon contact with the target.

In one embodiment of the invention, an off-the-shelf paintball gun can be used to deploy a "sensor-ball" which can be fired at a target some distance away to determine if the target contains threat or other detectable material. Such deployment can be accomplished from a safe standoff distance of several hundred meters. Fluid-filled compartments of the sensor-ball may contain suitable fluids to enhance the longevity of the immunosensor portion of the biosensor storage and protect the biosensor circuits during impact. For example, a sensor-ball deployed from a paintball gun may, upon hitting the target, have decelerating g-forces minimized by a colored fluid portion within one of the chambers absorbing the impact on an inner biosensor circuit. This fluid can also serve the purpose of initially marking the target to determine if proper placement has been achieved and fluid may be such as to allow the inner biosensor circuit to stick to the target.

In another detection embodiment, a network of communicating RFID/biosensors may be deployed from aircraft, vehicles or by individuals to aid in detection of threats. Such RFID/biosensors may be enclosed within transportable, suitably shaped units which permit simple positioning on most terrain to assure appropriate sampling of the surrounding environment. One embodiment may include an RFID/biosensor circuit having several acoustic wave (AW) immunosensors which activate upon impact, sample the surrounding vicinity and transmit back resulting information to either the operator or a receiver and display located on mobile or fixed positions, airborne or other surveillance vehicles. The information transmission method may be wireless, wires, light or sound. The target may be further identified for future action with the use of a read/write RFID.

In a derivation of the above embodiment, an active RFID/biosensor circuit sampling the environment and powered by an energy source such as a fuel cell, may use the by-products of the energy source, such as water and heat, to prolong the useful lifespan of the immunosensor within arid or colder environments.

An RFID/biosensor in accordance with the invention can:
(a) protect the biolayer while being stored prior to use,
(b) protect the unit during the impact of actual deployment,
(c) once deployed and within the field, improve the longevity of the biolayer by controlling the temperature and humidity,
(d) obtain very large standoff distances with a sensor network that need not be interrogated, including the concept of many personnel be able to detect the threat (as compared to searching for a needle in a haystack and placing a light or equivalent on the needle so that everyone can see it).

The invention is well suited for the determination of improvised explosive devices (IEDs), abandoned or suspect packages, shipping containers, vehicles or any other object that may contain a threat. The deployment of the RFID/biosensor using a paintball gun would be easy for most first responders, who would use this invention for detecting explosive biological or other chemical substances. This invention can detect threats at the intended target. This invention can also easily confirm by means of a marking fluid that the intended target was contacted. The affordable cost of the total system in accordance with the invention can make it acceptable for wide integration within military, law enforcement or commercial sectors. A sensor-ball can be of the same caliber as that of commercially sold paintball guns. The user would purchase the specific type of sensor-balls to detect biological explosives, drugs or other chemical substances.

Other uses of this invention may include both agricultural and military examples where roadways or large areas of inaccessible locations would be tested for chemical or biological substances. This would include being able to test for bacteria and micro-organisms or other chemical molecules without being physically intrusive to the crops or land by distributing the biosensors using several means, including paint-ball guns, vehicles, aircraft or individuals. Such detection of chemical and biological molecules using an RFID/biosensor would be well suited for use with the invention described by Stubbs et al. "DETECTION OF SIGNALING MOLECULES IN A BIOLOGICAL ENVIRONMENT" U.S. patent application Ser. No. 11/226,261 filed Sep. 15, 2005, the contents of which are hereby incorporated herein by reference.

This invention permits a real-time, safe, low cost yet accurate deployment method of a biosensor which can determine the status of a possible IED or other biological or chemical threats. In a preferred embodiment, the user would be able to determine at a safe distance of several hundred meters the status of a possible threat. The distance is more of a function of the deployment means, such as the quality of the paintball gun and the accuracy of the user aiming the deployment gun or position of the deploying aircraft or vehicles. In another embodiment, a network of RFID/biosensors can be distributed along a known route or area several days ahead of time and each time the route is traveled the RFID/biosensors can be interrogated for the detection of possible threats. This scenario would provide detection times in the sub-second range at distances of several hundred meters. As standoff distances are increased to hundreds of meters, a system configuration can eliminate the need for interrogation of the device, and an alert such as a light emitting diode (LED) attached to the RFID/biosensor system can then allow all personnel to receive the alert and detect the threat.

The longevity of the immunosensor can be extended within arid and colder environments by the use of by-products such as heat and moisture from a fuel cell powering the biosensor.

DESCRIPTION OF THE DRAWINGS

Embodiments of the invention will now be described, by way of example, with reference to the accompanying drawings, of which.

DESCRIPTION OF PREFERRED EMBODIMENTS

Figure 1:
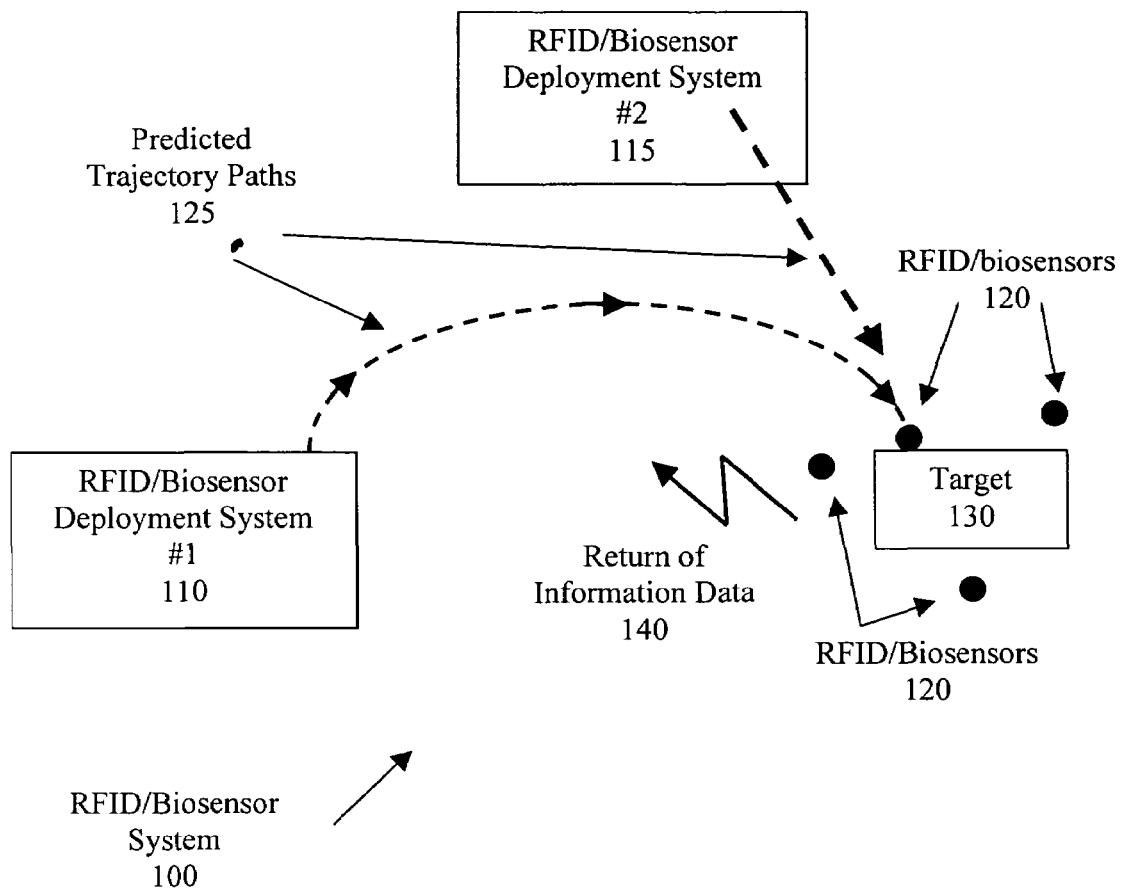
FIG. 1 is a diagrammatic view of an RFID/biosensor ball being deployed to a target.

Referring to the drawings, FIG. 1 shows an RFID/biosensor system 100 having a first RFID/biosensor deployment system 110 and a second RFID/biosensor deployment system 115 which can launch RFID/biosensors 120 along predicted trajectory paths 125. The RFID/biosensor deployment system 110 may utilize a COTS paintball gun with a suitable caliber to match that of the RFID/biosensor 120. Such paintball guns can be equipped with COTS laser sites to improve the accuracy of the aim. The RFID/biosensor deployment system 115 may deploy RFID/biosensors 120 from an aircraft to an intended target 130. The target 130 may be a roadway, a large tract of land, buildings or individual objects, including animate objects. Alternatively, the RFID/biosensors 120 may be deployed from land vehicles or by simply positioning them manually. When an RFID/biosensor 120 makes impact with the intended target 130, a sequence of events take place. Upon impact, the RFID/biosensor 120 is activated, samples the surrounding space and then changes certain parameters of the RFID/biosensor 120 if a threat substance is detected. This change in parameters indicating a potential threat is either embedded within the information data 140 and is returned back to the user to assist in determining further action or activates an internal alert which can be received by users in up to several hundred meters away.

The RFID/biosensor 120 has different fluid-containing chambers which perform several functions. These will now be summarized and will be described in more detail later. The fluid in the outer chambers reduces the deceleration force on the actual biosensor components. This fluid may also leave an identifying mark if required to indicate the accuracy of the placement to user. This fluid may also be tacky enough to keep the RFID/biosensor component from ricocheting off the target 130. The fluid in inner chambers assist in preserving the longevity and improving the storage duration of the immunosensor.

An RFID/biosensor 200 in the form of a ball in accordance with one embodiment of the invention and which can be deployed from a COTS paint-ball gun will now be described with reference to FIG. 2. The RFID/biosensor ball 200 has a protective outer layer 210 which is strong enough to permit reliable handling thereof but which is weak enough to cause breakage of the outer layer 210 upon impact with the target 130.

A fluid outer portion 220 of the RFID/biosensor-ball 200 has several functions. Its primary function is to minimize the decelerating g-forces on both an internally located biosensor circuit 240 and ancillary circuitry located on circuit support modules 250. The fluid outer portion 220 includes a number of various selected chambers or compartments 222 which contain several different fluids or a mixture thereof to serve the purpose of initially marking the target 130 to determine if proper placement was achieved. Such fluids are also selected to be of predetermined texture and consistency to cause the biosensor circuit 240 and circuit support modules 250 to stick to the target 130. The fluid outer portion 220 has numerous membrane supports 225 located to provide structural support. The membranes 225 also aid in minimizing decelerating g-forces on both the biosensor circuit 240 and ancillary circuitry located on the circuit support modules 250 and serve in breaking the protective outer layer 210 upon impacting the target 130.

A protective inner layer 211 securely encloses a fluid inner portion 230 which improves the immediate environment of an immunosensor layer in the biosensor circuit 240. This contains substances such as polyethylene glycol (PEG), which is a non-conducting polymer which forms a bio-shield. PEG has already been used to enhance the characteristics of biosensors, Berney et al, "A differential capacitive biosensor using polyethylene glycol to overlay the biolayer", Sensors and Actuators Vol. B44, pp. 578-584, 1997, and Salmaso et al, "Preparation and characterization of active site protected poly(ethylene glycol)-avidin bioconjugates", BIOCHEMICA ET BIOPHYSICA ACTA, available online at www.sciencedirect.com, 2005. The PEG bio-shield associates with water molecules surrounding immobilized antibodies in the immunosensor, thus masking their surface from absorptive interactions. In addition, flexible PEG chains can readily adapt their configuration to fit the surface topology of the immobilized antibodies. This bio-shield then serves the purpose of protecting the biolayer from enzyme degradation, pH and temperature changes. PEG in solution does not form covalent bonds with the biolayer, but forms a quasi-adsorbed overlayer. This overlayer of PEG solution can be rinsed away by including a phosphate buffered saline (PBS) solution within various selected compartments 222 located within both the fluid inner portion 230 and the fluid outer portion 220. This PBS/Tween (ph 7.4) solution will provide a rinsing action to remove the PEG solution prior to any sensing action of the biolayer.

Figure 2:
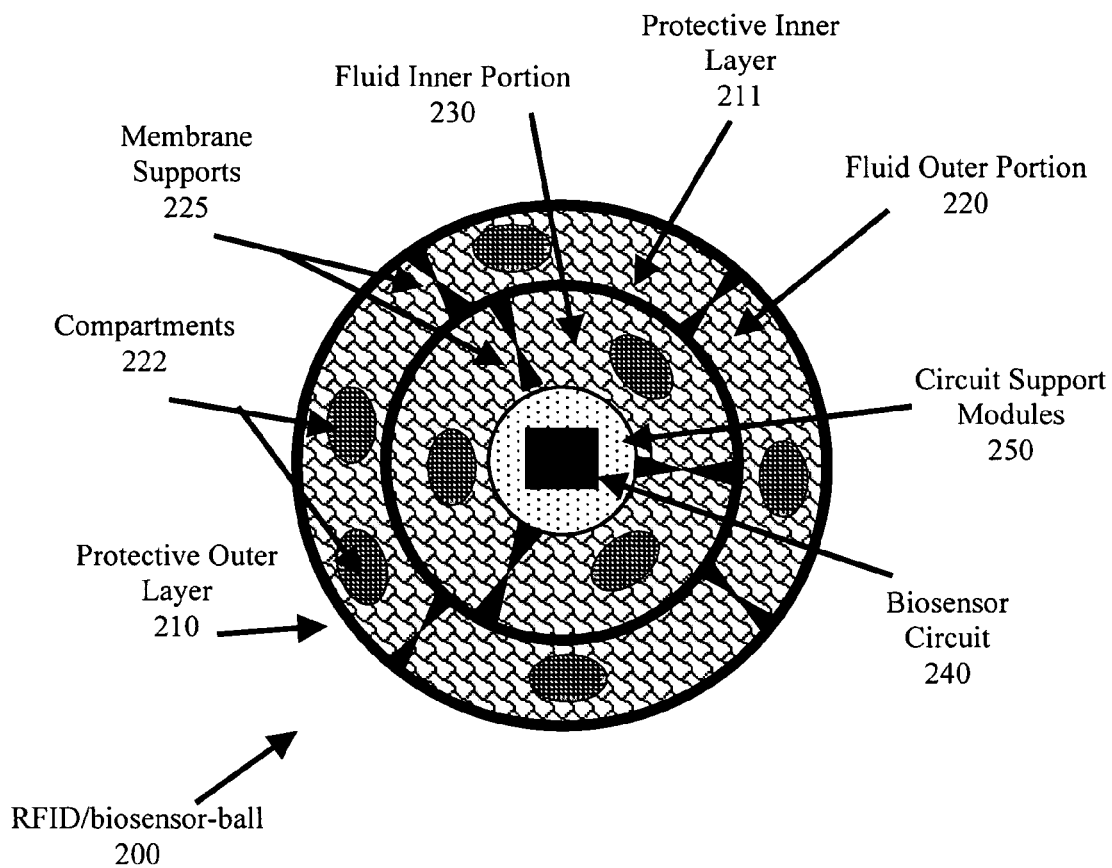
FIG. 2 is a diagrammatic sectional view of an RFID/biosensor ball in accordance with one embodiment of the invention.

Although the RFID/biosensor ball 200 illustrated in FIG. 2 has a spherical shape, it may be of any shape appropriate for deployment from a discharge tube, the barrel of a gun or deployment by other means such as by dropping large numbers from an airborne device.

Figure 3:
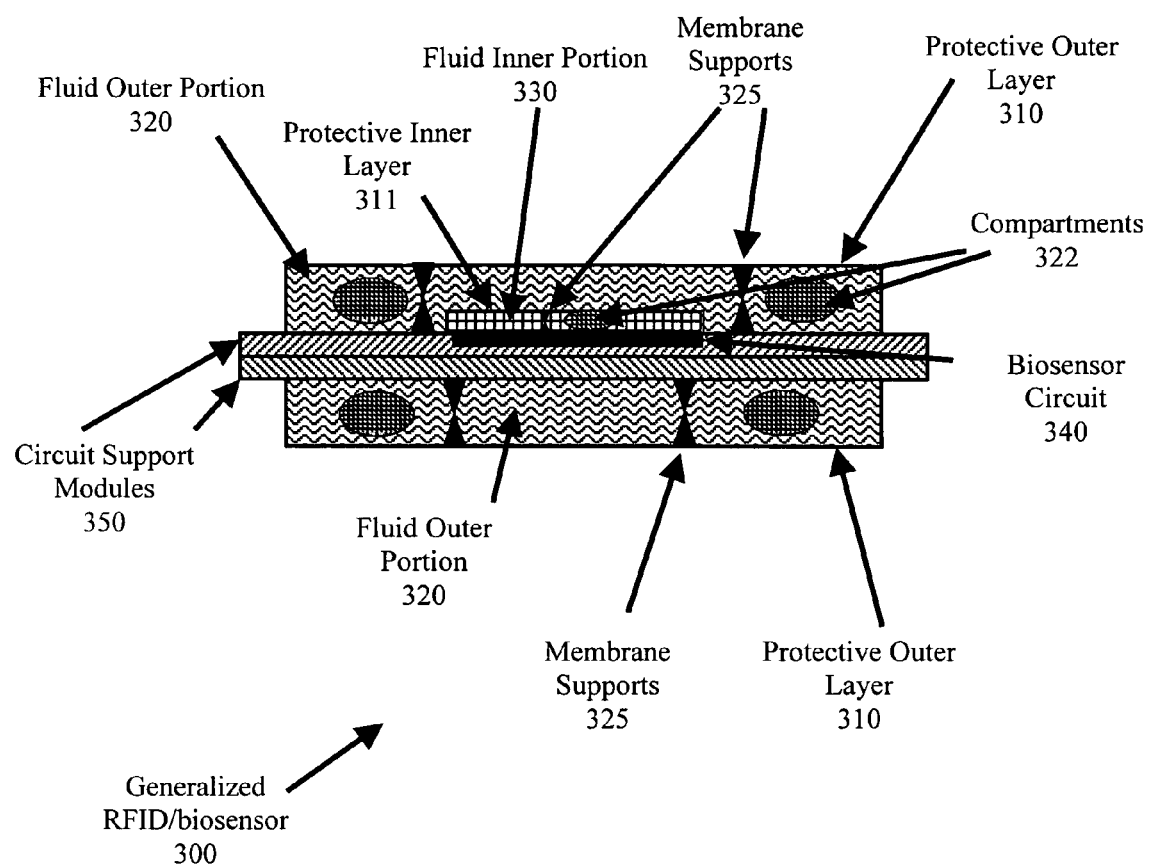
FIG. 3 is a similar view of an RFID/biosensor assembly in accordance with another embodiment.

An RFID/biosensor 300 in accordance with another embodiment of the invention will now be described with reference to FIG. 3. This embodiment is useful for deployment from an aircraft by deployment system 115 shown FIG. 1. The RFID/biosensor 300 may have an aerodynamic shape to minimize impact effects when dropped from a height vertically. The function and purpose of the components of the RFID/biosensor 300 shown in FIG. 3 are similar to those of the RFID/biosensor-ball 200 shown in FIG. 2. The protective outer layer 310, protective inner layer 311, fluid outer portion 320, compartments 322, membrane supports 325, fluid inner portion 330, biosensor circuit 340 and circuit support modules 350 all have the same function and purpose as the comparable components shown in FIG. 2. Larger membrane supports 325 are located in the fluid outer portion 320, with smaller ones being located in the fluid inner portion 330.

Figure 4:
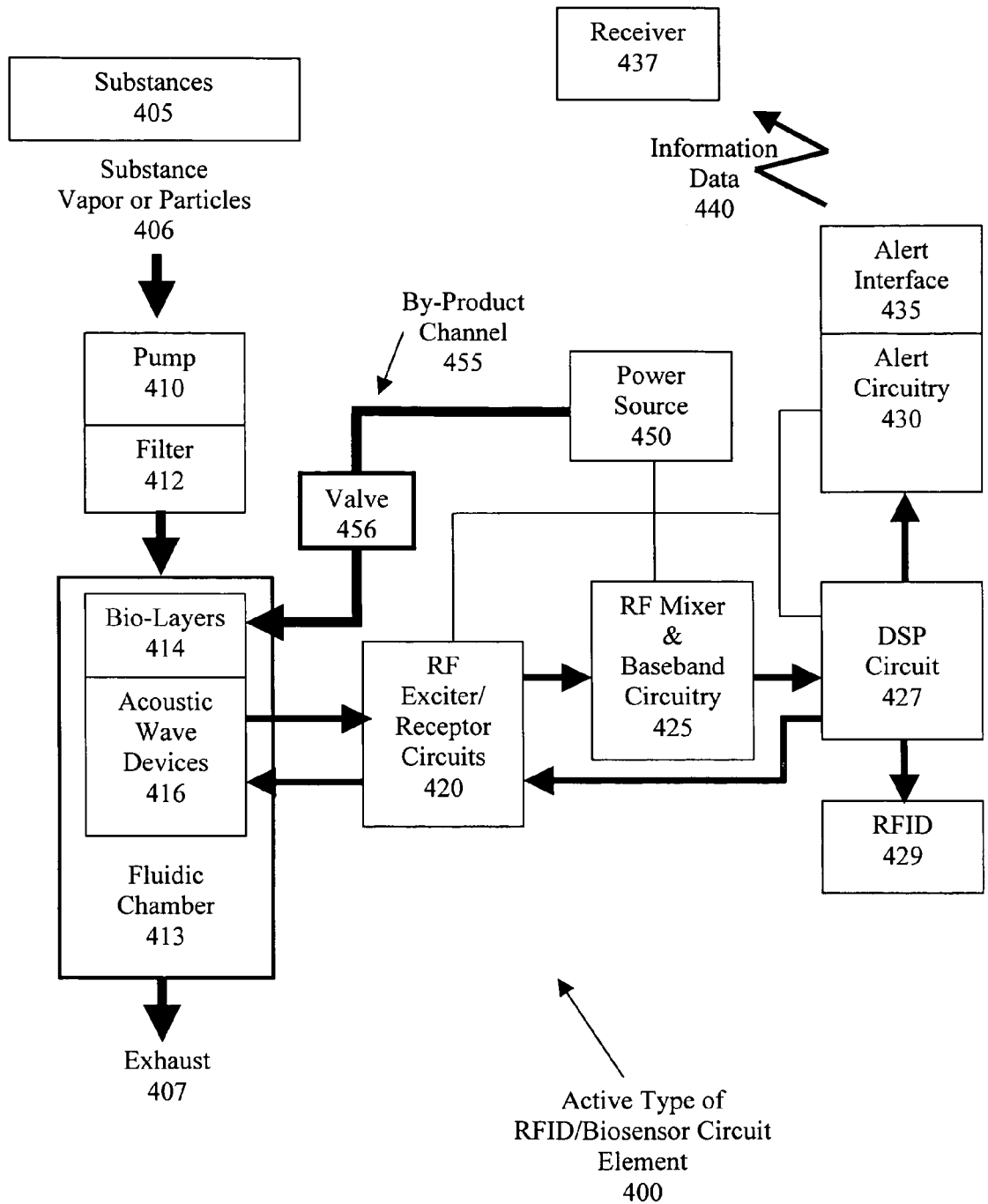
FIG. 4 is a block diagram of an active type RFID/biosensor circuit.

The RFID/biosensor 200 or the RFID/biosensor 300 may have an active type RFID/biosensor circuit 400 as shown in FIG. 4. An active type of RFID/biosensor circuit includes a circuit whose main source of energy is derived from a device such as a battery, super-cap or other charge-producing device, including fuel cells or solar cells connected to the circuit. This source of energy is then used to provide energy to components of the RFID/biosensor circuit 400 such as pumps, RF and baseband circuitry, microprocessors and various alerts.

FIG. 4 shows substances 405 which are close enough to the functional components of the RFID/biosensor circuit to be detected. Trace amounts of substance vapors or particles 406 suspended in the air or fluid will diffuse close to or be drawn towards the RFID/biosensor circuit 400 by means of a pump 410. A filter 412 removes unwanted particles and the substance vapors or particles 406 flow into a fluidic chamber 413 and come into contact with the biolayer portion 414 positioned on an acoustic wave device 416, both of which are situated within the fluidic chamber 413 with the RFID/biosensor circuit 400. An exhaust 407 then completes the flow path.

The biolayer 414 may be made by immobilizing a monolayer of antibodies on the surface of an acoustic wave (AW) device 416 (Sang-Hun Lee et al "Vapor Phase Detection of Plastic Explosives Using a SAW Resonator Immunosensor Array" Proceedings IEEE Sensor Symposium, 2005). The drying effect on an antibody molecule within the biolayers 414 is such that the structural fidelity of an antibody entrapped in the hydrogel therein is determined by the amount of water molecules associated with the molecule. As the environment in a cross-linker-antibody biolayer begins to dry, the tertiary structure of the protein begins to collapse and the binding activity of the antibody declines. It is therefore essential to maintain moisture within the hydrogel layer using moisture produced within the active type of RFID/biosensor circuit element 400. The temperature effect must also be considered because antibodies are very stringent molecules which are known to resist temperatures of up to 40° C. The optimum temperature of antibodies is from 2° C. to 40° C., i.e. before the onset of various structural changes in the folding motifs of the molecule. The antibody folding structure is very specific and is responsible for the binding activity of the antibody.

The acoustic wave device 416 is electrically connected to an RF exciter/receptor circuit 420 which is controlled by the digital signal processor (DSP) circuit 427. The acoustic wave device 416, with the biolayer 414 attached, generates a signal centered about its natural frequency. This natural frequency can vary depending on the acoustic wave device 416 used and can vary from tens of MHz to the GHz range. Such circuitry has been described (W. D. Hunt et al "Time-dependent signatures of acoustic wave biosensors," *IEEE Proceedings*, Vol. 91, no. 6, pp. 890-901, June 2003), (D. D. Stubbs, et al "Investigation of cocaine plumes using surface acoustic wave immunoassay sensors," *Analytical Chemistry*, vol. 75, no. 22, pp. 6231-6235, Nov. 15, 2003) and (Sang-Hun Lee et al "Real-Time Detection of Bacteria Spores Using a QCM Based Immunosensor," *Proceedings IEEE Sensor Symposium*, 2003).

As the vapors or small physical particles of the substance 405 suspended in the air or a fluid make contact with the biolayer 414 a change in the signal of acoustic wave device 416 occurs. Typically, more than one acoustic wave device 416 may be used and a multiplicity of biolayers 414 are present to detect multiple substances 405. An RF mixer and baseband circuit 425 follow the RF exciter/receptor circuit 420 to prepare and condition the signal of acoustic wave device 416 for signal processing within the DSP circuit 427. Processing and mapping of the possible threat substances within the DSP circuit 427 has been described by Edmonson et al. in DIFFERENTIATION AND IDENTIFICATION OF ANALOGOUS CHEMICAL OR BIOLOGICAL SUBSTANCES WITH BIOSENSORS, U.S. patent application Ser. No. 11/088,809 filed Mar. 25, 2005, the contents of which are hereby incorporated herein by reference. Notification back to the receiver 437 of this information data 440 which was processed and mapped within the DSP circuit 427 takes place via the alert circuit 430 and the alert interface 435. The receiver 437 may be either an animate or an intelligent device or both.

The alert interface 435 may present an audible signal, such as a sound which emits a code, a visual signal such as a bright LED which flashes a code or other signals incorporating RF and other parts of the frequency spectrum. A simple example which is consistent with a large standoff distance is an alert consisting of a visible light produced by an LED when the unit becomes operational. This has the advantage that observers who know that a roadway or other area has been seeded with RFID/biosensors can confirm that they have not been tampered with or wrongly removed. Such an alert can be coded so that the coded light source transmits an operational code and then, when a threat is detected, transmits the type and level of threat concentration detected in a different coded alert. The observers may be personnel who are in a position to observe the LED source from safe distances. The alert interface 435 may also be configured to include wired, wireless or audible connectivity which connects the receiver 437 with the active type RFID/biosensor circuit element 400.

A separate RFID 429 with read/write capabilities may also store the information data 440 for assessment at a future time when the active type biosensor circuit 400 has terminated its sensing, processing and alert capabilities. The RFID 429 provides for the interrogation and retrieval of the information data 140 stored therein and for the outcome of the detection process to be made available for up to several years after the sensing process. This separate RFID 429 would be self-contained in that it would have its own antenna operable at some suitable frequency and be constructed using either semiconductor or acoustic wave technologies. A suitable power source 450 such as a battery, super capacitor, solar cell or fuel cell would provide the energy to operate the active type RFID/biosensor circuit element 400 for the expected lifetime of the operational process.

By-products such as heat and moisture from the operational power source 450 are channeled via a by-product channel 455 to the fluidic chamber 413 housing the biolayers 414 to improve their longevity. Fuel cells utilizing technologies such as Proton Exchange Membrane (PEM) have by-products of water ($H_2O$) and heat. Fuel cells utilizing technologies such as Direct Methanol (DM) have by-products of water ($H_2O$), carbon dioxide ($CO_2$) and heat. The temperatures of these by-products are typically about 90° C. for a PEM fuel cell and about 120° C. for a DM fuel cell. A valve 456 controls the amount of heated by-product that passes through by-product channel 455 in order to maintain an optimum temperature and humidity level within the fluidic chamber 413 housing the biolayers 414.

Figure 5:
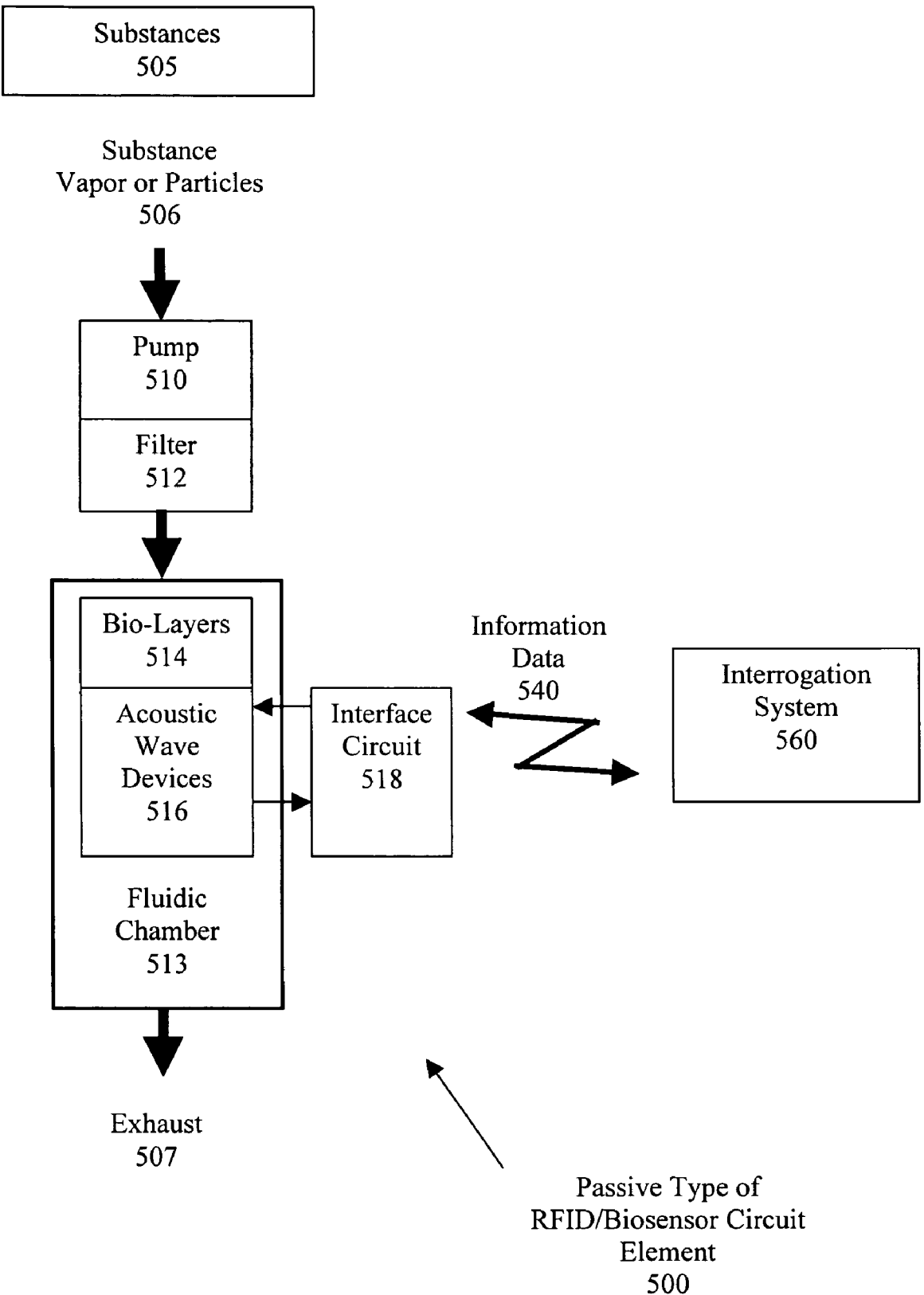
FIG. 5 is a similar view of a passive type of RFID/biosensor circuit.

An RFID/biosensor 200 or an RFID/biosensor 300 with a passive type RFID/biosensor circuit 500 will now be described with reference to FIG. 5. A passive type of biosensor circuit includes a circuit whose main source of energy is derived from an interrogation signal. FIG. 5 shows a substance 505 which is close enough to the functional components of the biosensor circuit 500 to be detected thereby. Trace amounts of substance vapors or particles 506 suspended in the air or fluid will diffuse close to or be drawn towards the RFID/biosensor circuit 500. A passive pump 510 operates in accordance with the blackbody process caused by thermally heating specific portions of the RFID/biosensor 500. When the surface of the thermally conductive structure immediately surrounding the volume containing the fluidic chamber 513 is blackened, it becomes a good absorber of radiation. This results in a localized rise of temperature, which will be accompanied by a decrease in density of the air or fluid within the volume containing the fluidic chamber 513. This less dense medium will be replaced through convection processes by a medium of greater density. This greater density medium then flows through a filter 512 that would remove unwanted particles to eliminate contamination, and the vapors or small physical particles of the substance 506 then enter the fluidic chamber 513 and come into contact with the biolayer portion 514 residing on the acoustic wave device 516 of the RFID/biosensor circuit 500. An exhaust 507 then completes the flow path.

The arrangement of biolayer 514 on the surface of the acoustic wave device 516 is similar to that described, namely by immobilizing a monolayer of antibodies on the surface of an acoustic wave (AW) device 516 (Sang-Hun Lee et al "Vapor Phase Detection of Plastic Explosives Using a SAW Resonator Immunosensor Array" *Proceedings IEEE Sensor Symposium*, 2005). The acoustic wave device 516 is electrically connected to an interface device 518. This interface device 518 is an electrical circuit, the nature of which depends on the means of interrogation by an interrogation system 560. For RF wireless configurations, the interface device 518 would be an RF antenna. The frequency of this antenna would be the same as the operating frequency of the acoustic wave device 516 and the interrogation system 560. For other wireless systems, the interface device 518 would be a suitable electrical circuit capable of receiving the interrogation signal and responding in a proper fashion back to the interrogation system 560 with the information data 540. For a wired system, the interface device 518 would electrically connect the acoustic wave device 516 with the interrogation system 560. Such a passive type RFID/biosensor circuit element 500 has been described by Edmonson et al., A SURFACE ACOUSTIC WAVE SENSOR OR IDENTIFICATION DEVICE WITH BIOSENSING CAPABILITY, U.S. patent application Ser. No. 11/139,477 filed May 31, 2005 and previously mentioned. The interrogation system 560 could also posses the capabilities of processing, mapping and alerting of the possible threat substances within its own DSP and alert circuitry.

In a preferred embodiment, the interface circuit 518 would contain an antenna structure constructed on a material which would structurally breakdown within a certain time period when exposed to certain environments such as moisture and sunlight. This structural breakdown would then compromise the mechanical attachment to which the RF antenna is attached and render the RF antenna inoperative. Thus preventing the RF antenna from receiving or transmitting back the interrogation signal. This disabling of the passive type RFID/biosensor circuit element 500 would coincide with the demise of the biolayer. The usefulness of such a disabling operation is that it would prevent false returns from future interrogation signals when new, fresh passive type RFID/biosensor circuits 500 are distributed in the same area.

The active type RFID/biosensor circuit element 400 or passive type RFID/biosensor circuit element 500 would may have an aerodynamic design to minimize impact effects and may have a construction such that, when the devices are positioned in the field, they can be camouflaged as rocks, sticks or other objects to minimize discovery by opponents.

The advantages of this invention will now be readily apparent to a person skilled in the art from the foregoing description of preferred embodiments. Other embodiments will also now be readily apparent. The scope of the invention being defined by the appended claims.

The invention claimed is:

1. A deployable acoustic wave RFID/biosensor assembly having:
   at least one protective layer,
   an acoustic wave RFID/biosensor within the protective layer or layers,
   said acoustic wave RFID/biosensor including:
      an acoustic wave device,
      a biolayer mounted on the acoustic wave device,
      an electrical circuit operable to actuate the acoustic wave device, and
      a fluidic chamber associated with the biolayer and which in use contains fluid which, if a predetermined substance to be sensed is present, operates to modify the biolayer which in turn affects the operation of the acoustic wave device, and
   protective fluid within the protective layer or layers substantially surrounding the acoustic wave RFID/biosensor to protect the acoustic wave RFID/biosensor from damage when the RFID/biosensor assembly impacts a target and to protect the biolayer from deterioration during storage and use.

2. An RFID/biosensor assembly according to claim 1 wherein said at least one protective layer comprises a protective outer layer containing protective fluid to protect the acoustic wave RFID/biosensor from damage when the RFID/biosensor assembly impacts the target, and a protective inner layer containing protective fluid which protects the biolayer from deterioration during storage and use.

3. An RFID/biosensor assembly according to claim 2 wherein the protective outer and inner layers are substantially spherical.

4. An RFID/biosensor assembly according to claim 2 wherein the protective outer layer is adapted to rupture when the RFID/biosensor assembly impacts a target to cause leak of protective fluid therefrom, and said leaking fluid is selected such that it causes the RFID/biosensor assembly to adhere to the target.

5. An RFID/biosensor assembly according to claim 1 wherein the acoustic wave RFID/biosensor includes a power source to provide power for the electrical circuit and which in use improves the temperature and/or humidity environment of the biolayer.

6. An RFID/biosensor assembly according to claim 1 wherein the acoustic wave RFID/biosensor includes a blackbody radiator to provide a passive convectional pump which causes fluid in the fluidic chamber to pass over the biolayer.

7. An RFID/biosensor assembly according to claim 1 and having an aerodynamic shape which, when the RFID/biosensor assembly is deployed, causes the RFID/biosensor assembly to follow a predicted trajectory path to an intended target.

8. A method of deploying an RFID/biosensor assembly in accordance with claim 1 comprising discharging the RFID/biosensor assembly from the barrel of a gun.

* * * * *